US012629254B2

(12) United States Patent
Fiedler et al.

(10) Patent No.: US 12,629,254 B2
(45) Date of Patent: May 19, 2026

(54) AUGMENT ELEMENT FOR KNEE PROSTHESIS

(71) Applicant: Limacorporate S.p.A., San Daniele del Friuli (IT)

(72) Inventors: Christoph Fiedler, Diekhof (DE); Massimo Ceconi, Travesio (IT); Marta Martelossi, Gradisca d'Isonzo (IT); Michele Pressacco, Martignacco (IT)

(73) Assignee: Limacorporate S.p.A., San Daniele del Friuli (IT)

( * ) Notice: Subject to any disclaimer, the term of this patent is extended or adjusted under 35 U.S.C. 154(b) by 626 days.

(21) Appl. No.: 18/080,551

(22) Filed: Dec. 13, 2022

(65) Prior Publication Data

US 2023/0114476 A1 Apr. 13, 2023

Related U.S. Application Data

(62) Division of application No. PCT/EP2021/068511, filed on Jul. 5, 2021.

(51) Int. Cl.
*A61F 2/30* (2006.01)
*A61F 2/38* (2006.01)

(52) U.S. Cl.
CPC ...... *A61F 2/30734* (2013.01); *A61F 2/30767* (2013.01); *A61F 2/3859* (2013.01);
(Continued)

(58) Field of Classification Search
CPC ........ A61F 2/30734; A61F 2002/30736; A61F 2002/30217; A61F 2002/30594; A61F 2/3859
See application file for complete search history.

(56) References Cited

U.S. PATENT DOCUMENTS 4,961,748 A 10/1990 Frey et al.
7,291,174 B2 11/2007 German et al.
(Continued)

FOREIGN PATENT DOCUMENTS

CN 107820414 A 3/2018
WO 2013/134333 A1 9/2013
(Continued)

OTHER PUBLICATIONS

International Search Report dated Sep. 23, 2021, issued in connection with PCT/EP2021/068511.
(Continued)

*Primary Examiner* — Javier G Blanco
(74) *Attorney, Agent, or Firm* — Eversheds Sutherland (US) LLP

(57) ABSTRACT

Augment element for knee prosthesis, comprising a metal body of a substantially truncated conical shape configured to be inserted into a bone extremity and having an outer surface comprising a metal trabecular surface. The metal body being hollow with an axial through-cavity defining a plurality of substantially annular transversal sections. The metal body is inclined in a direction of inclination, so as to define at least one eccentricity between a first transversal section at a first end of the axial through-cavity and a second transversal section at a second end of the axial through-cavity. The augment element further comprises a plurality of through-slits in the metal body, open from the first end up to an intermediate portion on the metal body, wherein the plurality of through-slits is configured for a radial compression of the metal body, locally reducing a circumference of the substantially annular transversal sections during insertion of the augment element, and increasing a press-fit towards a bone portion.

11 Claims, 10 Drawing Sheets

(52) U.S. Cl.
CPC ..... *A61F 2/389* (2013.01); *A61F 2002/30115* (2013.01); *A61F 2002/30217* (2013.01); *A61F 2002/30736* (2013.01); *A61F 2002/30738* (2013.01); *A61F 2002/30777* (2013.01); *A61F 2002/3092* (2013.01)

(56) References Cited

U.S. PATENT DOCUMENTS

| | | | | |
|---|---|---|---|---|
| 9,149,282 | B2 | 10/2015 | Servidio et al. | |
| 2005/0004679 | A1* | 1/2005 | Sederholm | A61F 2/36 623/22.46 |
| 2006/0147332 | A1 | 7/2006 | Jones et al. | |
| 2008/0262626 | A1* | 10/2008 | Raugel | A61F 2/30734 623/22.15 |
| 2010/0253130 | A1 | 10/2010 | Sollami | |
| 2011/0009974 | A1 | 1/2011 | Blaylock et al. | |
| 2013/0231744 | A1* | 9/2013 | Taylor | A61B 17/16 623/16.11 |
| 2014/0277528 | A1* | 9/2014 | Mines | A61F 2/30734 623/20.14 |
| 2014/0277567 | A1 | 9/2014 | Collazo et al. | |
| 2018/0140424 | A1* | 5/2018 | Dees | A61F 2/389 |
| 2019/0015215 | A1* | 1/2019 | Marlow | A61F 2/38 |
| 2019/0070008 | A1 | 3/2019 | Bauer et al. | |

FOREIGN PATENT DOCUMENTS

| | | | |
|---|---|---|---|
| WO | 2015/145348 | A1 | 10/2015 |
| WO | 2016/183439 | A1 | 11/2016 |

OTHER PUBLICATIONS

Written Opinion of the International Searching Authority dated Sep. 23, 2021, issued in connection with PCT/EP2021/068511.

Implantcast GmbH. Mutars® Epore®: Sistema universal modular—Conos universales corticales y metafisarios: Técnica quirúrgica. 2019. implantcast GmbH.

LimaCorporate S.p.A. Trabecular Titanium™: Advanced cellular solid structure for cementless orthopaedic implants. 2013. LimaCorporate S.p.A.

Ohlmeier, M. et al., "Preliminary clinical results of coated porous tibia cones in septic and aseptic revision knee arthroplasty", Arch. Orthop. Trauma Surgery, 2021, 141(4): pp. 555-560.

"TrabecuLink Cones" [Video]. 2019. Youtube. https://www.youtube.com/watch?v=FXD_pw0pMq0&t=5s.

Waldemar Link España. "Mr. Ridhian Morgan-Jones / Zones & Cones [LINK Webinar]" [Video]. 2020. Youtube. https://www.youtube.com/watch?v=ME70SxVGHqw.

Waldemar Link GmbH & Co. KG. directLINK: Magazin für Endoprothetik. 2018. Waldemar Link GmbH & Co. KG.

Waldemar Link GmbH & Co. KG. TrabecuLink® Tibiakonen: Operationstechnik. 2018. Waldemar Link GmbH & Co. KG.

Waldemar Link GmbH & Co. KG. TrabecuLink® Tibiakonen: Produktflyer. 2018. Waldemar Link GmbH & Co. KG.

Waldemar Link GmbH & Co. KG. TrabecuLink® Tibiakonen: Produktinformation. 2018. Waldemar Link GmbH & Co. KG.

* cited by examiner

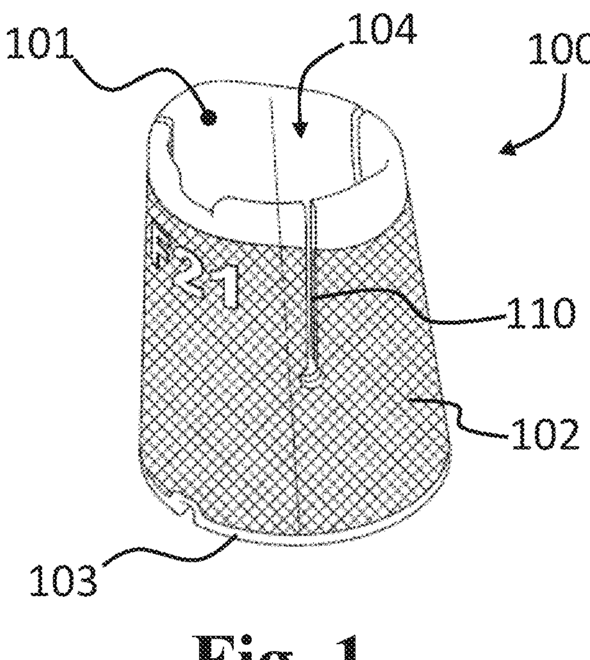
Fig. 1
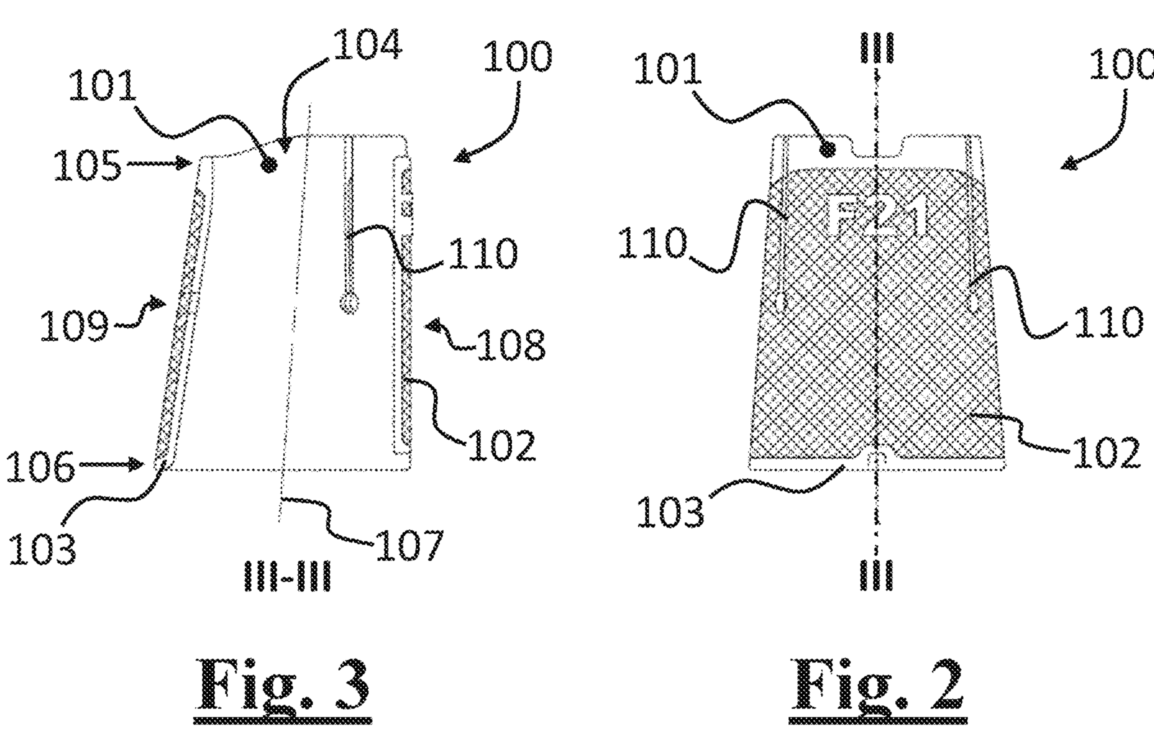
Fig. 3
Fig. 2

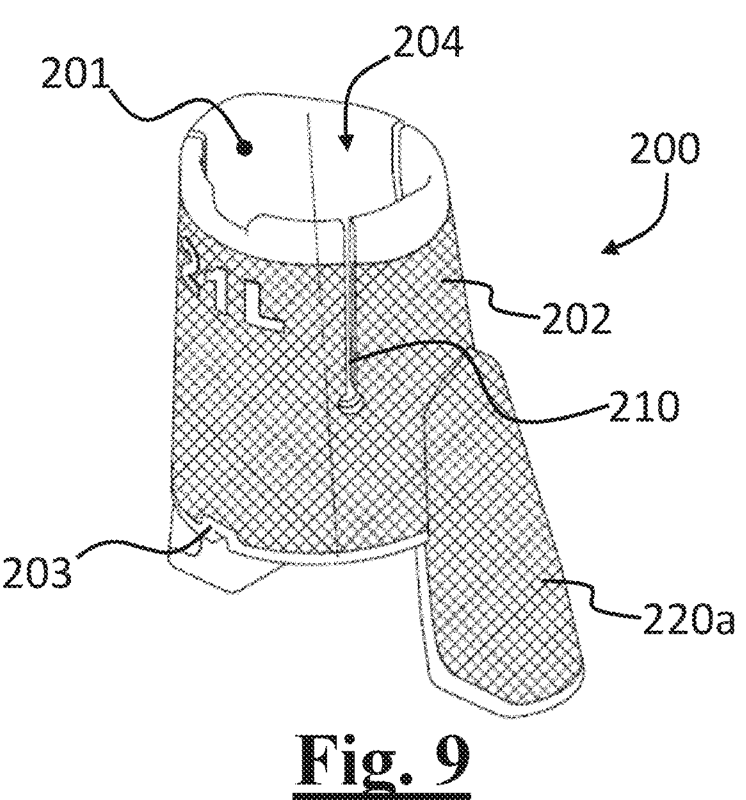
Fig. 9
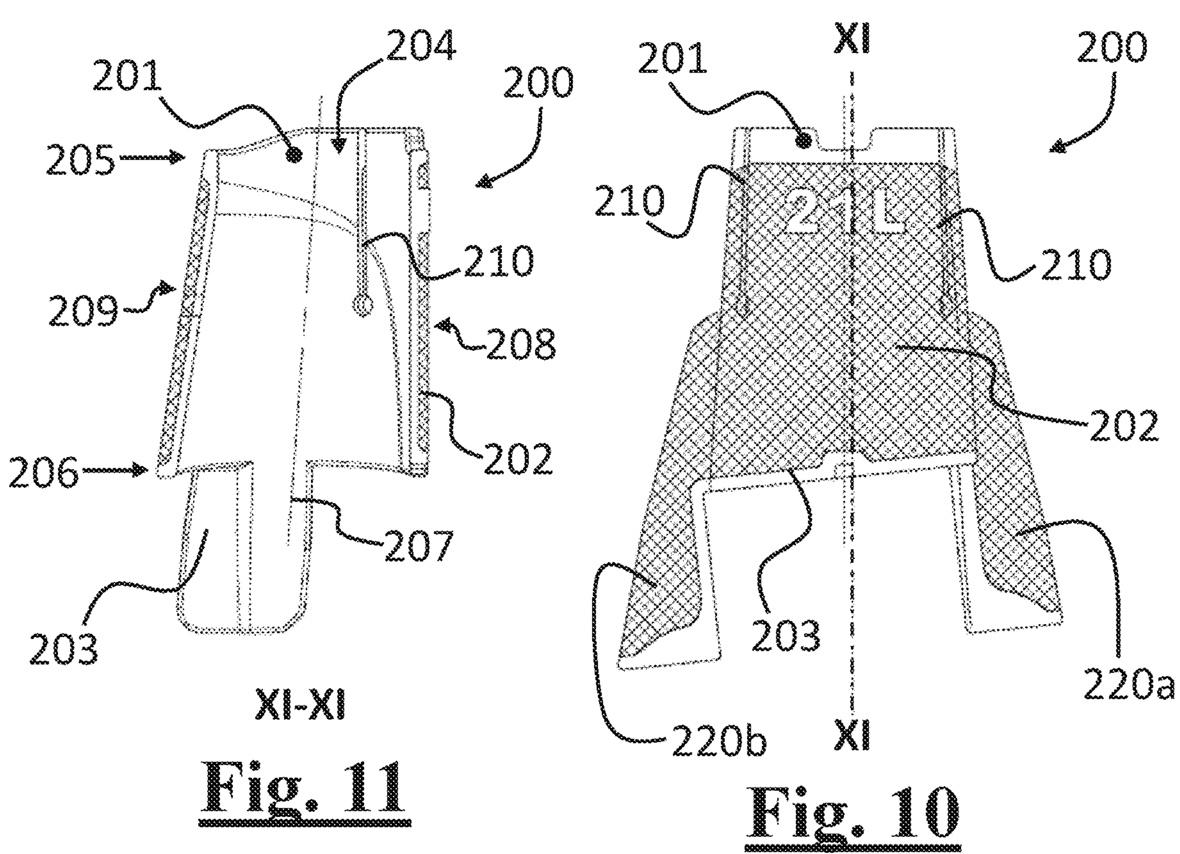
Fig. 11
Fig. 10

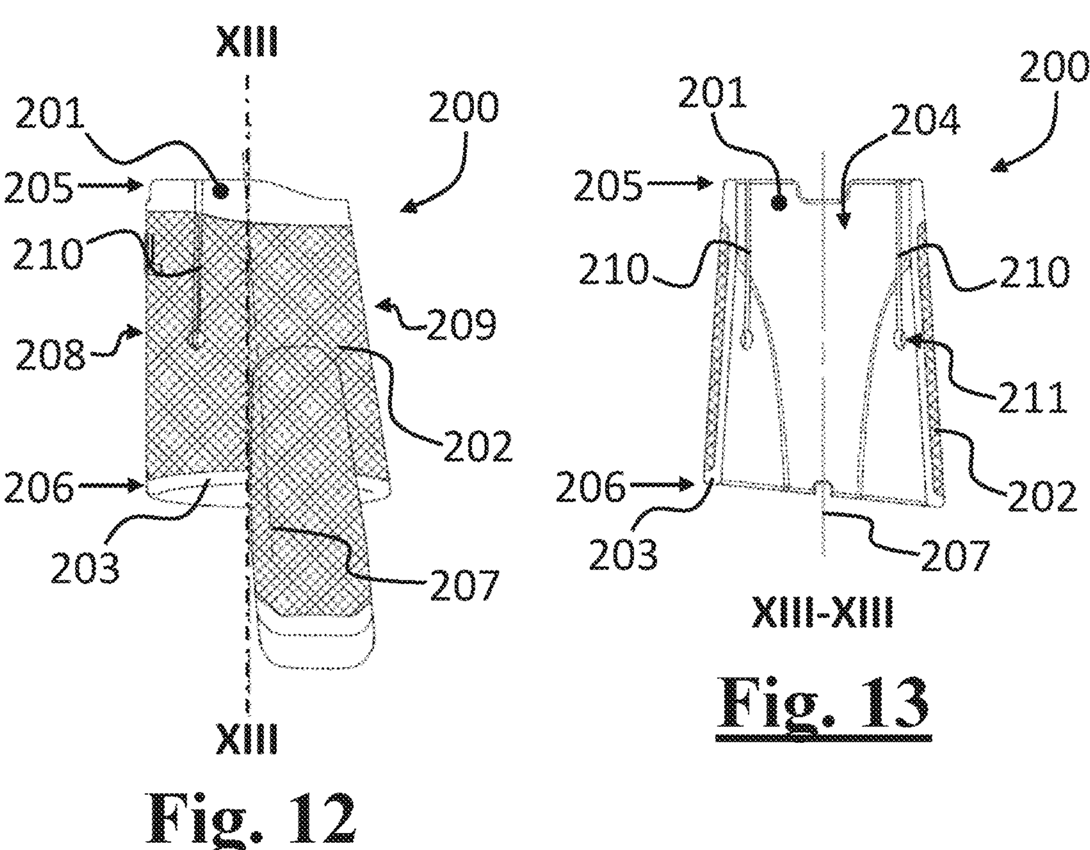
Fig. 12
Fig. 13
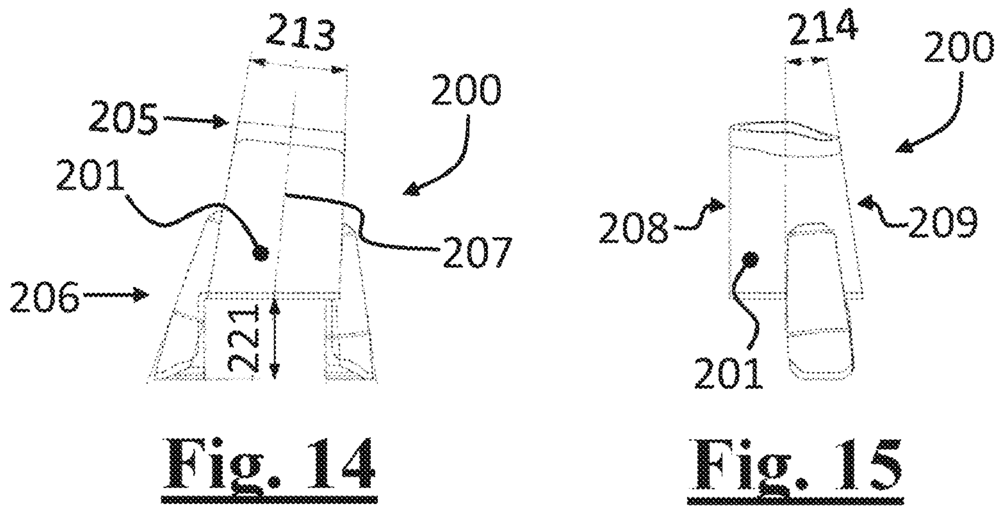
Fig. 14
Fig. 15

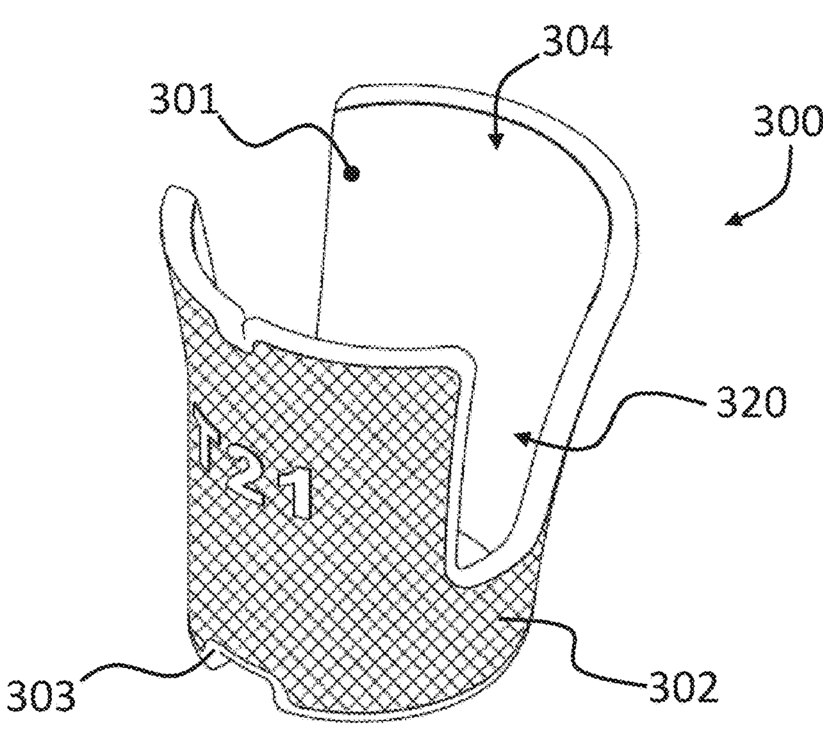
Fig. 16
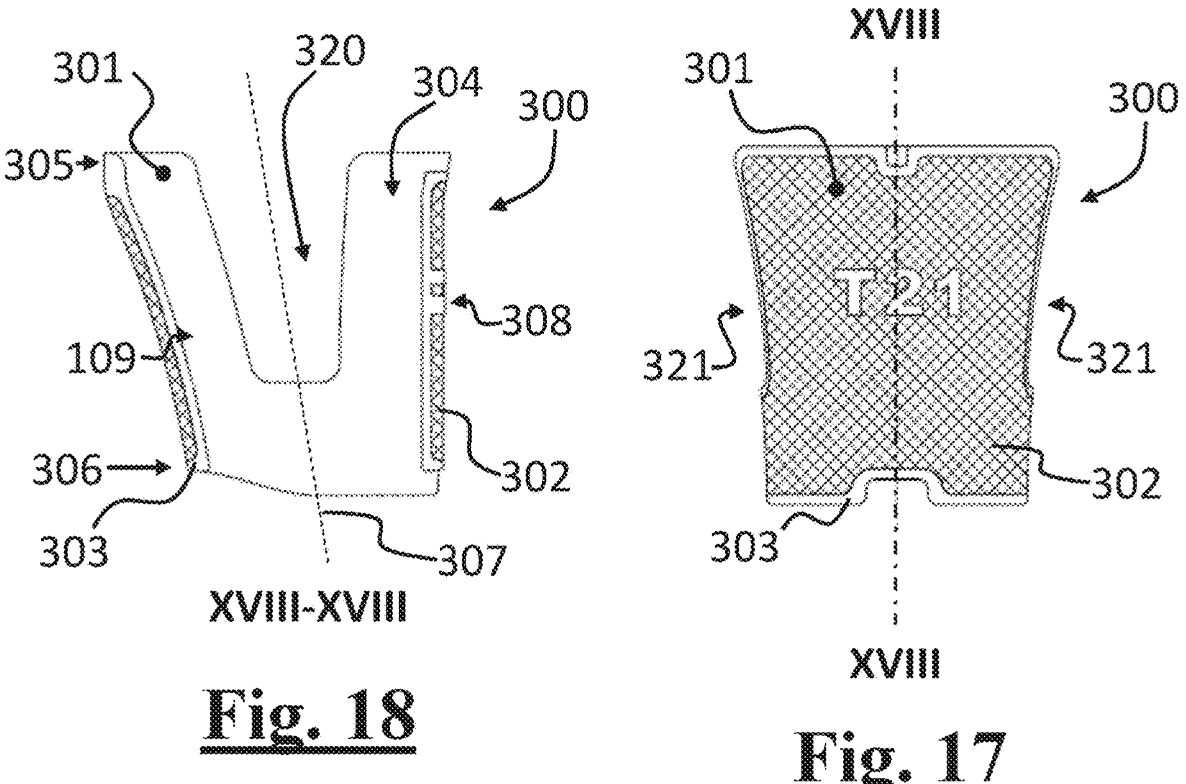
Fig. 18
Fig. 17

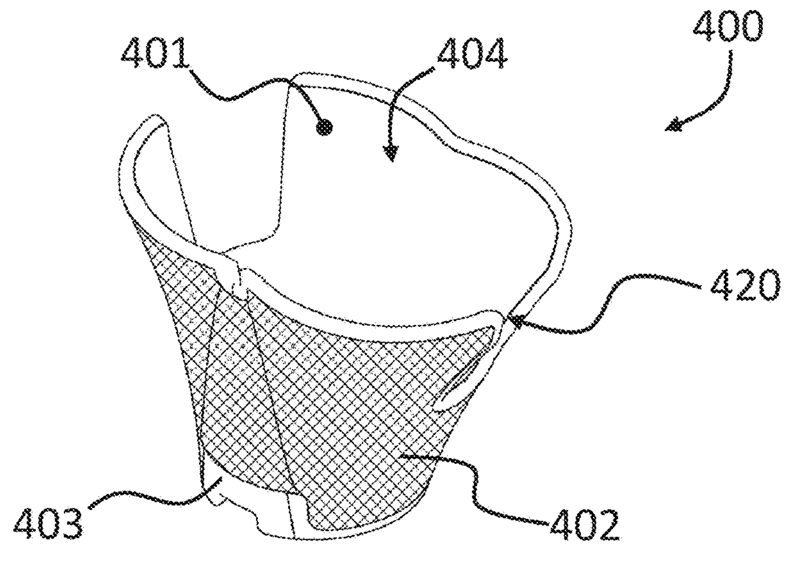
Fig. 24
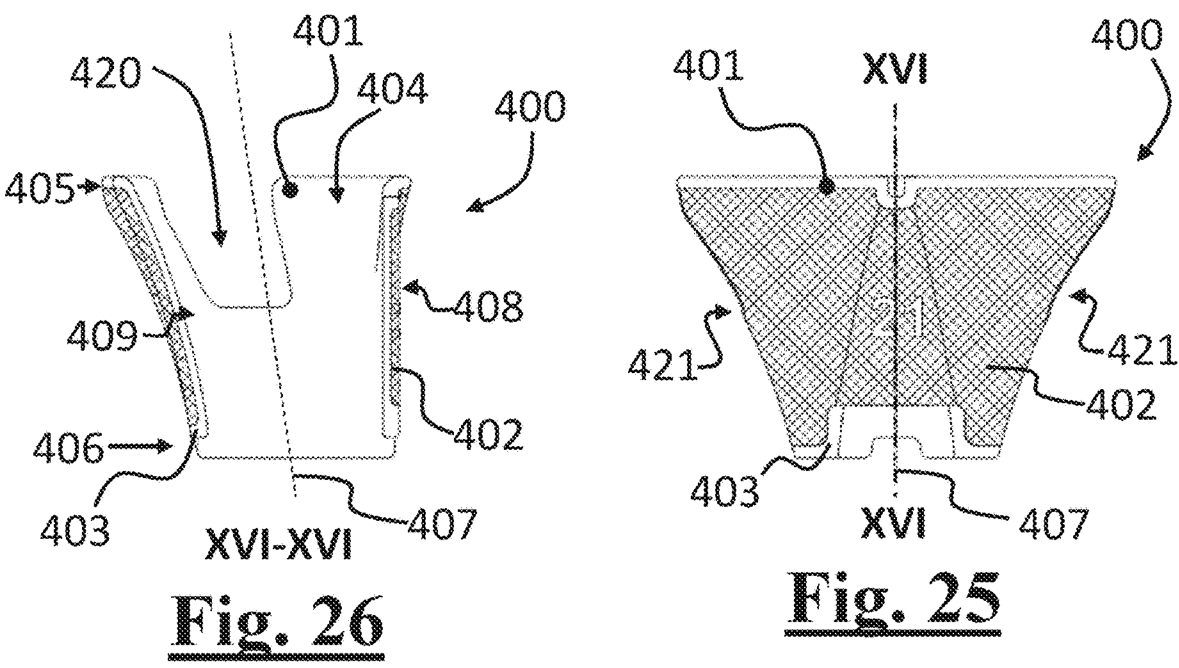
Fig. 26
Fig. 25

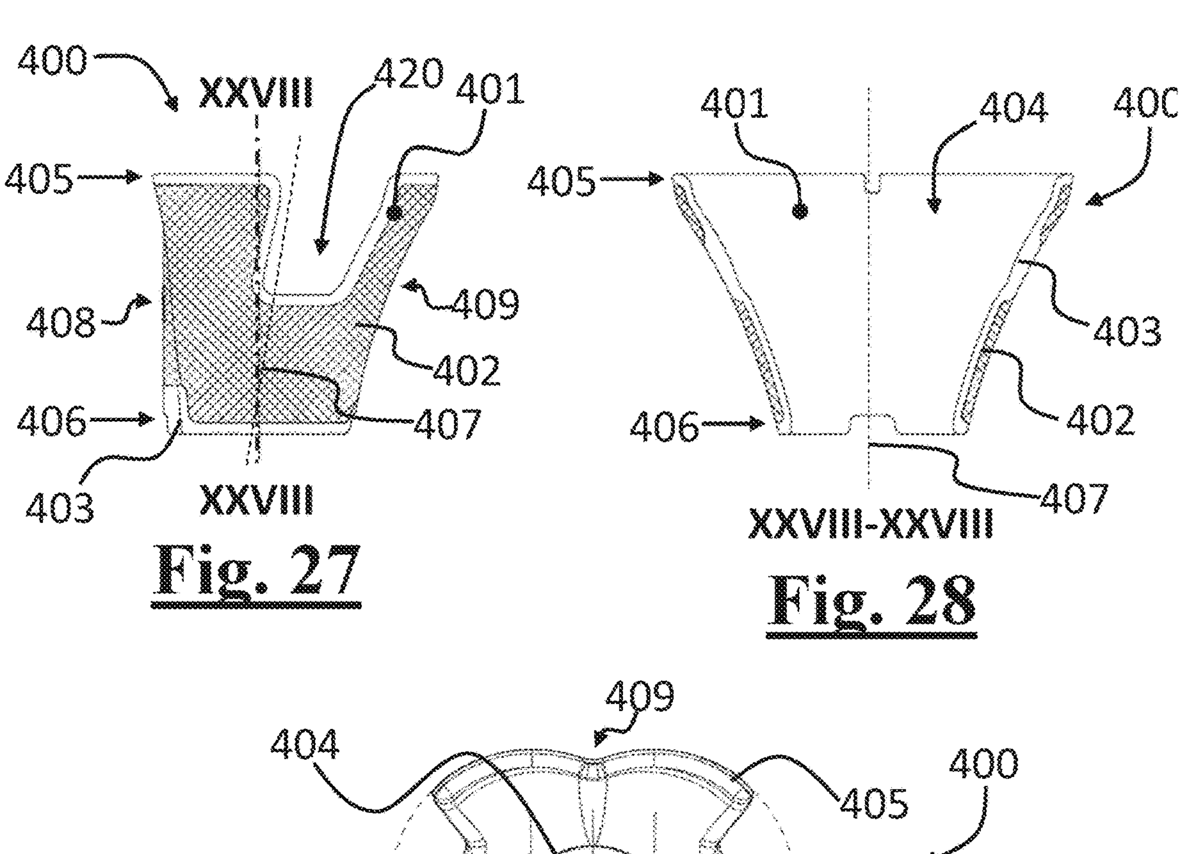
Fig. 27
Fig. 28
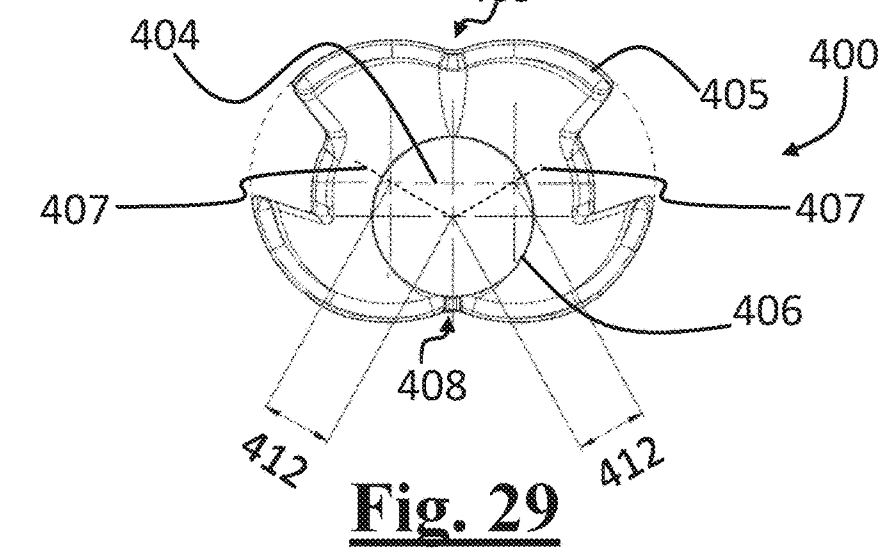
Fig. 29
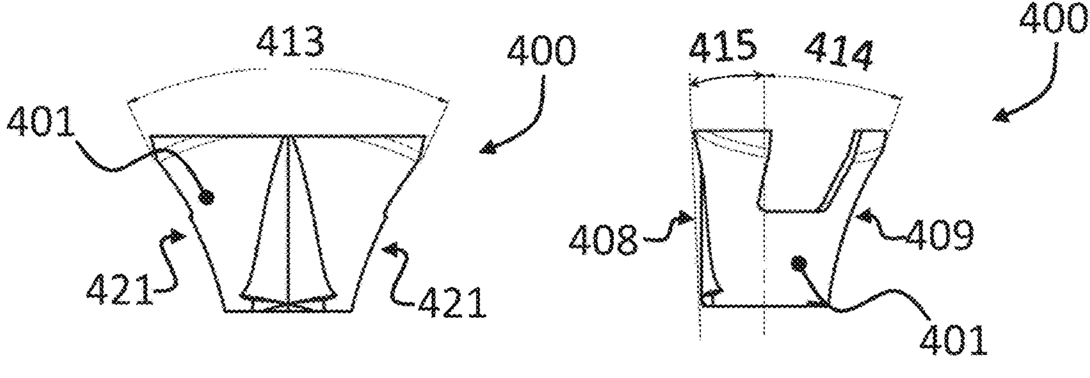
Fig. 30
Fig. 31

420
401
404
400′
410
411
402
403

AUGMENT ELEMENT FOR KNEE PROSTHESIS

CROSS-REFERENCE TO RELATED APPLICATIONS

This application is a divisional of PCT/EP2021/068511, filed Jul. 5, 2021, and claims priority to Italian Patent Application No. 102020000016288, filed Jul. 6, 2020, the entire contents of both of which are hereby incorporated by reference.

FIELD OF APPLICATION

The present invention refers to an augment element for prosthesis comprising a metal body of a substantially truncated conical shape configured to be inserted in a bone extremity.

The invention is particularly useful in the surgical interventions of knee prosthesis implantation and the following description is made with reference to this specific field of application in order to simplify the exposition thereof.

In general, it is not excluded that the present invention could be applied in other types of surgical interventions of prosthesis implantation in bone extremities.

PRIOR ART

In the orthopaedic surgery for the implantation of a prosthesis, a bone seat is sometimes subjected to the application of an augment element, typically applied in a housing milled in the bone with a desired profile.

In the context of the present description, with the term "augment element" is meant a prosthesis element capable of filling or taking the place of a bone portion cut or degraded due to pre-existing pathologies or implantations and further capable of being connected to further prosthesis joint elements in order to provide a stable implantation.

The usage of an augment element is particularly common when a spongy part of the bone is not able to support by itself the prosthesis, especially in the case of knee or hip prosthesis.

Typically, an augment element is a substantially cone-shaped or truncated cone-shaped component made of metal.

For example, a knee prosthesis typically comprises a femoral component which is fixed to the distal extremity of a femur, and a tibial component which is fixed to the proximal extremity of a tibia. In that case, both an augment element for the extremity of the femur, and an augment element for the extremity of the tibia can be provided.

The document WO2015/145348 (A1) relates to a multi-layered augment element for prosthesis, comprising a body of truncated conical shape with an axial through-cavity open at both ends and an annular section. The body comprises an outer portion of metal trabecular material.

The document US2019/070008 (A1) relates to an augment element for prosthesis, comprising a hollow sleeve with an internal channel which crosses it. The hollow sleeve comprises one or more bending joints, configured for compressing the channel and reducing the circumference and width of the hollow sleeve. The body is of metal material, without trabecular portions.

A difficulty which emerges in the prior art is that the known augment elements are not able to precisely correspond with the bone anatomy, thus making the performances of the implanted prosthesis unsatisfactory.

In particular, since both tibia and femur have an asymmetric elongated configuration, known augment elements are not able to match the specific tibial or femoral bone anatomy of the patient.

Furthermore, in the prior art, there are problems regarding the insertion or removal of augment elements in the respective bone seat, which involve surgical complexity or difficulty.

A general object of the present invention is to provide to the surgeon an augment element which solves some drawbacks of the prior art.

A further object of the present invention is to allow an augment element to better adapt to the specific bone anatomy.

A further object of the present invention is to provide an augment element particularly suitable for a specific tibial or femoral bone anatomy of a patient.

A further object of the present invention is to give an augment element which is more efficient during insertion or removal in the respective bone seat.

SUMMARY OF THE INVENTION

The solution idea underlying the present invention is to provide an augment element for prosthesis configured to be inserted in a bone extremity, having a metal body of a substantially truncated shape with an axial cavity. The metal body has a plurality of annular sections defined along the axial cavity, which are eccentrically stacked so as to define a global inclination of the metal body. The configuration of the metal body allows to better adapt to the specific bone anatomy, in particular for femoral or tibial applications. Additionally, a metal trabecular surface, preferably obtained in one piece and seamlessly with the metal body, can be provided to further improve implantation and attachment on the bone seat.

Based on such solution idea, an augment element for prosthesis, in particular for knee prosthesis, is provided which comprises a metal body of a substantially truncated conical shape and configured to be inserted in a bone extremity. The body has an outer surface preferably comprising a metal trabecular surface. The metal body is hollow with an axial through-cavity defining a plurality of substantially annular transversal sections. Furthermore, the metal body is inclined in a direction of inclination, so as to define at least one eccentricity between a first transversal section at a first end of the axial through-section and a second transversal section at a second end of the axial through-cavity.

Thereby, an augment element particularly suitable for a specific asymmetric bone anatomy is provided, with particular advantage in case of application of the augment element to a tibial or femoral bone extremity.

It is also provided that the augment element for prosthesis has a metal body of a substantially truncated conical shape, with an axial through-cavity and comprising a metal trabecular surface. Preferably, the augment element further comprises a plurality of through-slits, open from a first end of the metal body up to an intermediate portion; such slits are configured for a radial compression of the metal body, thus locally reducing a circumference of the substantially annular transversal section of the metal body.

Thereby, an augment element is advantageously provided which is more efficient during the insertion and implantation, allowing a radial compression of the metal body which increases the press-fit toward the bone; together with the increasing of the press-fit towards the bone, also the pressure of the trabecular surface against the bone increases, thus stimulating the bone growth in order to ensure a stable and long-term connection.

The augment element according to the present invention advantageously improves both the primary stability and the secondary stability of the implantation. The primary stability is the one which is immediately observable in the intervention, it is practically a mechanic wedging. The secondary stability is instead obtained due to the osseointegration, which is improved by the presence of primary stability, by the presence of a trabecular structure or with adequate porosity and by the presence of a compression force or press-fit which stimulates the bone growth.

Furthermore, specific features of the augment element are provided which make it particularly efficient in case of applications to tibial or femoral extremities, which will be illustrated in detail in the following.

Further features and advantages of the invention will become apparent from the detailed description which follows, provided for illustrative and non-limiting purposes, and from the claims which form an integral part of the present description.

BRIEF DESCRIPTION OF THE DRAWINGS

FIG. 1 shows a prospective view of a first embodiment of augment element for prosthesis according to the present invention.

FIG. 2 shows a frontal view of the first embodiment of augment element for prosthesis.

FIG. 3 shows a lateral sectional view of the first embodiment of augment element for prosthesis.

FIG. 4 shows a lateral view of the first embodiment of augment element for prosthesis.

FIG. 5 shows a frontal sectional view of the first embodiment of augment element for prosthesis.

FIG. 6 shows a bottom view of the first embodiment of augment element for prosthesis.

FIG. 7 shows a frontal view of the first embodiment of augment element for prosthesis with further geometrical indications.

FIG. 8 shows a lateral view of the first embodiment of augment element for prosthesis with further geometrical indications.

FIG. 9 shows a prospective view of a second embodiment of augment element for prosthesis according to the present invention.

FIG. 10 shows a frontal view of the second embodiment of augment element for prosthesis.

FIG. 11 shows a lateral sectional view of the augment element for prosthesis.

FIG. 12 shows a lateral view of the second embodiment of augment element for prosthesis.

FIG. 13 shows a frontal sectional view of the second embodiment of augment element for prosthesis.

FIG. 14 shows a frontal view of the second embodiment of augment element for prosthesis with further geometrical indications.

FIG. 15 shows a lateral view of the second embodiment of augment element for prosthesis with further geometrical indications.

FIG. 16 shows a prospective view of a third embodiment of augment element for prosthesis according to the present invention.

FIG. 17 shows a frontal view of the third embodiment of augment element for prosthesis.

FIG. 18 shows a lateral sectional view of the third embodiment of augment element for prosthesis.

FIG. 19 shows a lateral view of the third embodiment of augment element for prosthesis.

FIG. 20 shows a frontal sectional view of the third embodiment of augment element for prosthesis.

FIG. 21 shows a frontal view of the third embodiment of augment element for prosthesis with further geometrical indications.

FIG. 22 shows a lateral view of the third embodiment of augment element for prosthesis with further geometrical indications.

FIG. 23 shows a top view of the third embodiment of augment element for prosthesis.

FIG. 24 shows a prospective view of a fourth embodiment of augment element for prosthesis according to the present invention.

FIG. 25 shows a frontal view of the fourth embodiment of augment element for prosthesis.

FIG. 26 shows a lateral sectional view of the fourth embodiment of augment element for prosthesis.

FIG. 27 shows a lateral view of the fourth embodiment of augment element for prosthesis.

FIG. 28 shows a frontal sectional view of the fourth embodiment of augment element for prosthesis.

FIG. 29 shows a top view of the fourth embodiment of augment element for prosthesis.

FIG. 30 shows a frontal view of the fourth embodiment of augment element for prosthesis with further geometrical indications.

FIG. 31 shows a lateral view of the fourth embodiment of augment element for prosthesis with further geometrical indications.

Figures 32, 33:
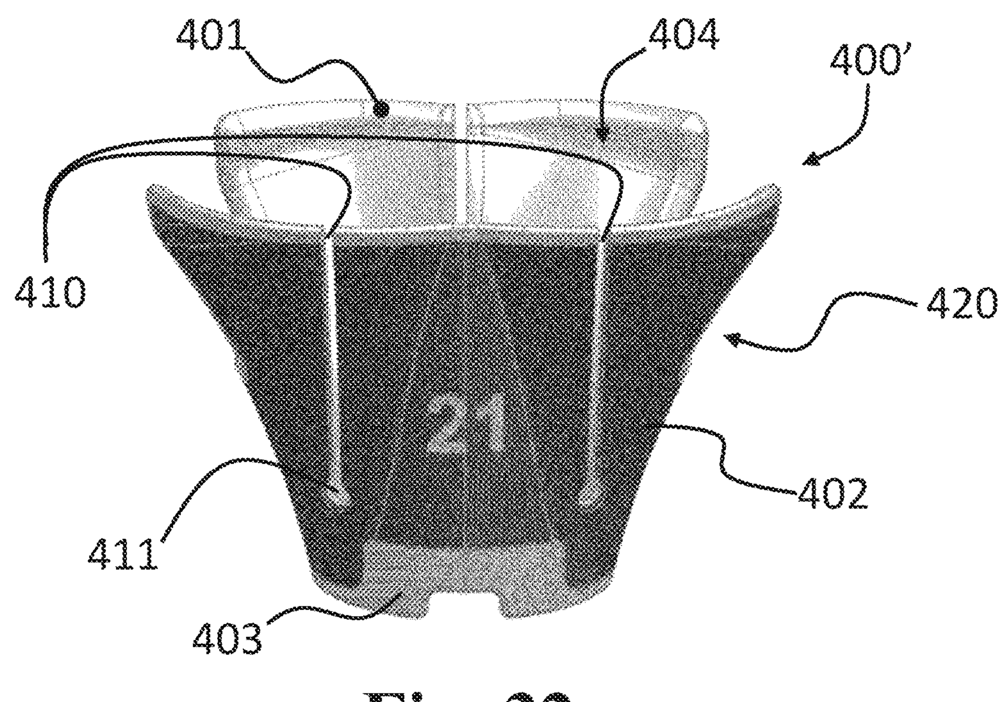
FIG. 32 shows a prospective view of a variation of the fourth embodiment of augment element for prosthesis.
FIG. 33 shows a further prospective view of a variation of the fourth embodiment of augment element for prosthesis.

In different figures, analogous elements will be indicated by analogous reference numbers.

The technical drawings presented in the figures are to be understood as purely illustrative, not necessarily made to scale or having the same scale among each other.

DETAILED DESCRIPTION

FIG. 1 shows a prospective view of a first embodiment of augment element 100 for prosthesis according to the present invention. The augment element 100 of this example is an element for femoral application, in combination with a knee prosthesis.

The augment element 100 comprises a metal body 101 of a substantially truncated conical shape, which is configured to be inserted in a femoral extremity. Preferably, the metal body 101 is made of titanium or alloys thereof, for biomedical applications.

In general, the metal body comprises walls, which will be further described, having a substantially constant thickness.

The metal body 101 has an outer surface comprising a metal trabecular surface 102; preferably the metal trabecular surface 102 is obtained in one piece seamlessly with the metal body 101 by a co-manufacture procedure, for example by EBM (Electron Beam Machining) technologies. A co-manufacture procedure in fact allows to provide an interface-free metal trabecular surface, so as to avoid the risk of detachments of the trabecular part of the metal body.

The metal body 101 preferably comprises a smooth edge 103 on the outer surface surrounding the metal trabecular surface 102 on one or more sides, preferably on all sides.

The metal body 101 is hollow with an axial through-cavity 104 defining a plurality of substantially annular transversal sections, whose configuration will be further described.

FIG. 2 shows a frontal view of the augment element 100 for prosthesis, wherein the two symmetric lateral walls of the same are shown, having a same inclination.

FIG. 3 shows a lateral sectional view of the augment element 100 for prosthesis, with respect to section III-III of FIG. 2.

The metal body 101 is inclined in a direction of inclination, in this case towards the right of the figure, so as to define an eccentricity between a first transversal section at a first end 105 of the axial through-cavity 104 and a second transversal section at a second end 106 of the axial through-cavity 104.

In particular, the axial cavity 104 has a longitudinal axis 107 inclined in the direction of inclination with respect to the vertical axis of the metal body 101. The vertical axis, not shown in the figure for the sake of simplicity, is perpendicular to one of the first or second transversal section, at the respective end 105 or 106.

The metal body 101 comprises a frontal wall 108 extended towards the direction of inclination, and a rear wall 109 opposite the frontal wall 108 and extended away from the direction of inclination.

The frontal wall 108 has an inclination with respect to the vertical axis that is less than an inclination of the rear wall 109.

In other words, the profile of the metal body 101 is tapered towards the first end 105, with a frontal asymmetry visible in lateral section.

Figures 4, 5, 6, 7, 8:
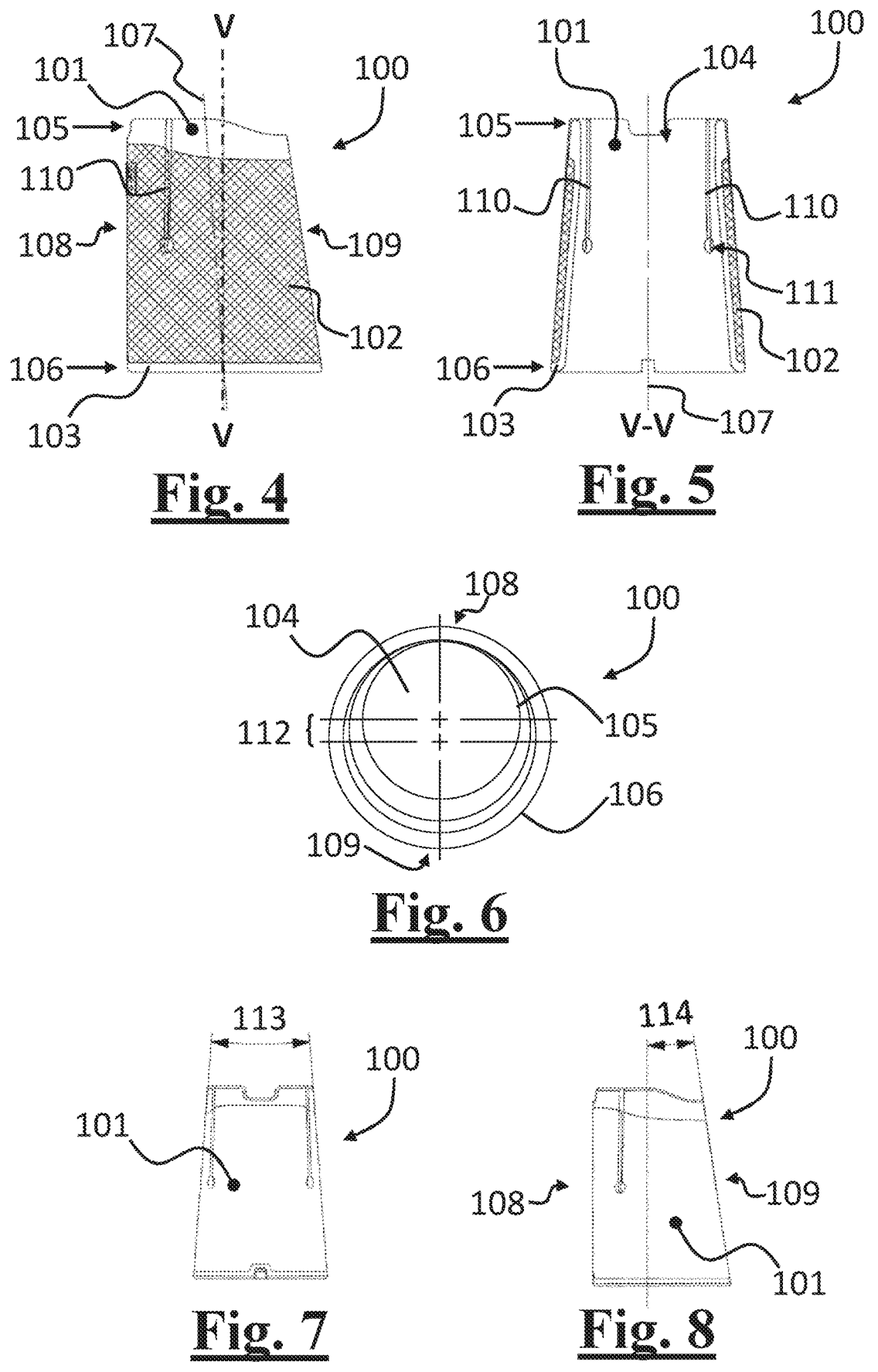

FIG. 4 shows a lateral view of the augment element 100 for prosthesis, wherein some features already discussed in relation to FIG. 3 are pointed out.

FIG. 5 shows a frontal sectional view of the augment element 100 for prosthesis, with respect to section V-V of FIG. 4.

In this embodiment, it is appreciated how the longitudinal axis 107 of the cavity 104 is instead not inclined with respect to a vertical axis of the metal body 101, considering the direction transversal to the direction of inclination shown in FIG. 3.

The augment element 100 further comprises a plurality of through-slits 110 in the metal body 101, which are open from the first end 105 up to an intermediate portion on the metal body 101.

These slits 110 are configured for a radial compression of the metal body 101, in particular facilitating the insertion in a femoral cavity, locally reducing a circumference of the substantially annular transversal sections which make up the metal body 101 during insertion of the augment element 100, and increasing a press-fit towards a bone portion.

In particular, for femoral applications, the first transversal section at the end 105 is smaller in size with respect to the second transversal section at the end 106, so as to facilitate an insertion of the metal body 101 into the femoral bone extremity.

Preferably, each of the slits 110 is open towards the first end 105 and ends in a respective enlarged circular hole 111 beside to the intermediate portion of the metal body 101. Thereby, the enlarged circular hole 111 is configured to improve a localized mechanical resistance of the metal body.

FIG. 6 shows a bottom view of the augment element 100 for prosthesis. In this view it is possible to appreciate the eccentricity 112 resulting between the first transversal (in this case, circular) section at the first end 105, and the second transversal (in this case, circular) section at the second end 106 of the axial through-cavity 104.

FIG. 7 shows a frontal view of the augment element 100 for prosthesis with geometrical indications relating to the metal body 101.

In particular, the conicity 113 of the symmetric lateral walls is overall comprised between 6° and 10°, more preferably equal to 8.5°.

FIG. 8 shows a lateral view of the augment element 100 for prosthesis with geometrical indications relating to the metal body 101.

In the example of the augment element 100, the frontal wall 108 is vertical that is with inclination of 0° with respect to the vertical. In general, an inclination of the frontal wall 108 with respect to the vertical axis can be comprised between 0° and 5°, more preferably comprised between 0° and 2°.

In the example of the augment element 100, the rear wall 108 has an inclination 114 of 8.5° with respect to the vertical. In general, an inclination of the rear wall 108 with respect to the vertical axis is comprised between 6° and 10°.

FIG. 9 shows a prospective view of a second embodiment of augment element 200 for prosthesis according to the present invention. The augment element 200 of this example is an element for femoral application, in combination with a knee prosthesis.

The augment element 200 comprises a metal body 201 of a substantially truncated conical form, which is configured to be inserted in a femoral extremity. Preferably, the metal body 201 is made of titanium or alloys thereof, for biomedical applications.

The metal body 201 has an outer surface comprising a metal trabecular surface 202; preferably the metal trabecular surface 202 is directly applied to the metal body 201 by a co-manufacture procedure in one piece and seamlessly, for example by EBM (Electron Beam Machining) technologies.

The metal body 201 preferably comprises a smooth edge 203 on the outer surface surrounding the metal trabecular surface 202 on one or more sides, preferably on all sides.

The metal body 201 is hollow with an axial through-cavity 204 defining a plurality of substantially annular transversal sections, whose configuration will be further described.

FIG. 10 shows a frontal view of the augment element 200 for prosthesis, wherein it is evident a pair of bicondylar supports 220*a* and 220*b*, arranged sideways in the metal body 201.

The bicondylar supports 220*a* and 220*b* protrude from a terminal transversal section of the body 201, and each comprises a tapered body, which widens away from the metal body 201.

Preferably, also the bicondylar supports 220*a* and 220*b* have an outer surface comprising a metal trabecular surface, made in one piece and seamlessly with the bicondylar supports 220*a* and 220*b*.

In the augment element 200, the bicondylar supports 220*a* and 220*b* perform a support function also for the femoral condyles, in case that the bone defect will be extended also to the latter. The choice between the embodiment 100 without bicondylar supports or 200 comprising the bicondylar supports of the augment element, may depend for example on the location and extension of the bone defect. For example, in case of a removal of an implantation with stem, there is often the generation of a femoral bone defect along the channel, for which it would be preferred to use an augment element 100 according to the first embodiment; differently, in case of advanced bone degeneration, a situation may arise where the femoral condyle will not offer sufficient support for a prosthesis, and it would be preferred to use an augment element 200 according to the second embodiment, in order to obtain a greater reinforcement of the area.

Preferably, the metal body comprises a smooth edge 203 on the outer surface, which surrounds at least partially the metal trabecular surface 202 and preferably also the metal trabecular surface of the bicondylar supports 220*a* and 220*b*.

FIG. 11 shows a lateral sectional view of the augment element 200 for prosthesis, with respect to section XI-XI of FIG. 10.

The metal body 201 is inclined in a direction of inclination, in this case towards the right of figure, so as to define an eccentricity between a first transversal section at a first end 205 of the axial through-cavity 204 and a second transversal section at a second end 206 of the axial through-cavity 204.

In particular, the axial cavity 204 has a longitudinal axis 207 inclined in the direction of inclination with respect to a vertical axis of the metal body 201. The vertical axis, not shown in the figure for sake of simplicity, is perpendicular to one of the first or second transversal section, at the respective end 205 or 206.

The metal body 201 comprises a frontal wall 208 extended towards the direction of inclination, and a rear wall 209 opposite the frontal wall 208 and extended away from the direction of inclination.

The frontal wall 208 has an inclination with respect to the vertical axis that is less than an inclination of the rear wall 209.

In other words, the profile of the metal body 201 is tapered towards the first end 205, with a frontal asymmetry visible in lateral section.

In fact, an eccentricity between the first transversal section at the first end 205, and the second transversal section at the second end 206 of the axial through-cavity 204 can be guessed.

FIG. 12 shows a lateral view of the augment element 200 for prosthesis, wherein some features already discussed in relation to FIG. 11 are pointed out.

FIG. 13 shows a frontal sectional view of the augment element 200 for prosthesis, with respect to section XIII-XIII of FIG. 12.

The augment element 200 further comprises a plurality of through-slits 210 in the metal body 201, which are open from the first end 205 up to an intermediate portion on the metal body 201.

These slits 210 are configured for a radial compression of the metal body 201, in particular facilitating the insertion in a femoral cavity, locally reducing a circumference of the substantially annular transversal sections which make up the metal body 201 during insertion of the augment element 200, and increasing a press-fit towards a bone portion.

In particular, for femoral applications, the first transversal section at the end 205 is smaller in size with respect to the second transversal section at the end 206, so as to facilitate an insertion of the metal body 201 into the femoral bone extremity.

Preferably, each of the slits 210 is open towards the first end 205 and ends in a respective enlarged circular hole 211 beside to the intermediate portion of the metal body 201. Thereby, the enlarged circular body 211 is configured to improve a localized mechanical resistance of the metal body.

In the augment element 200 for femoral applications, the first transversal section at the end 205 is smaller in size with respect to the second transversal section at the end 206, and the pair of bicondylar supports 220*a* e 220*b* arranged sideways protrude precisely from the second transversal section, thus being in distal position once the augment element is implanted in the respective femoral bone cavity.

FIG. 14 shows a frontal view of the augment element 200 for prosthesis with geometrical indications relating to the metal body 201.

In particular, the conicity 213 of the lateral walls is overall comprised between 6° and 10°, more preferably equal to 8.5° as in the example of the augment element 200.

As visible, the second transversal section at the end 206 is furthermore inclined in a second direction of inclination, in a plane transversal to the direction of inclination of the longitudinal axis 207. In that sense, the metal body 201 has a plane of inclination of the end 206 which is different with respect to the plane of inclination of the end 205, generating an overall asymmetry of the augment element 201, not only in the already-considered direction of frontal inclination, but also in a direction of transversal inclination of the whole metal body 201, visible in FIG. 14.

Furthermore, the pair of bicondylar supports 220*a* and 220*b* extends from the second end 206 by a same height 221, thus defining an asymmetric pair of bicondylar supports 220*a* and 220*b*.

In the light of the overall asymmetry of the augment element 200, it is clear that different solutions for a left or right femur must be provided.

FIG. 15 shows a lateral view of the augment element 200 for prosthesis with geometrical indications relating to the metal body 201.

In the example of the augment element 200, the frontal wall 208 is vertical that is with inclination of 0° with respect to the vertical. In general, an inclination of the frontal wall 208 with respect to the vertical axis can be comprised between 0° and 5°, more preferably comprised between 0° and 2°.

In the example of the augment element 200, the rear wall 209 has an inclination 214 of 8.5° with respect to the vertical. In general, an inclination of the rear wall 209 with respect to the vertical axis is comprised between 6° and 10°.

FIG. 16 shows a prospective view of a third embodiment of augment element 300 for prosthesis according to the present invention. The augment element 300 of this example is an element for tibial application, in combination with a knee prosthesis.

The augment element 300 comprises a metal body 301 of a substantially truncated conical shape, which is configured to be inserted in a tibial extremity. Preferably, the metal body 301 is made of titanium or alloys thereof, for biomedical applications.

The metal body 301 has an outer surface comprising a metal trabecular surface 302; preferably the metal trabecular surface 302 is directly applied to the metal body 301 by a co-manufacture procedure in one piece and seamlessly, for example by EBM (Electron Beam Machining) technologies.

The metal body 301 preferably comprises a smooth edge 303 on the outer surface surrounding the metal trabecular surface 302 on one or more sides, preferably on all sides.

The metal body 301 is hollow with an axial through-cavity 304 defining a plurality of substantially annular transversal sections, whose configuration will be further described.

In a natural analogy, the metal body 301 is similar to a flower corolla shape from which two opposed petals were removed.

FIG. 17 shows a frontal view of the augment element 300 for prosthesis, wherein the two symmetric lateral walls of the same are shown, having a same inclination and configuration.

FIG. 18 shows a lateral sectional view of the augment element 300 for prosthesis, with respect to section XVIII-XVIII of FIG. 17.

The metal body 301 is inclined in a direction of inclination, in this case towards the right of the figure, so as to define an eccentricity between a first transversal section at a first end 305 of the axial through-cavity 304 and a second transversal section at a second end 306 of the axial through-cavity 304.

In particular, the axial cavity 304 has a longitudinal axis 307 inclined in the direction of inclination with respect to a vertical axis of the metal body 301. The vertical axis, not shown in the figure for the sake of simplicity, is perpendicular to one of the first or second transversal section, at the respective end 305 or 306.

The metal body 301 comprises a frontal wall 308 extended towards the direction of inclination, and a rear wall 309 opposite the frontal wall 308 and extended away from the direction of inclination.

The frontal wall 308 has an inclination with respect to the vertical axis that is less than an inclination of the rear wall 309.

In other words, the profile of the metal body 301 is tapered towards the second end 306, with a frontal asymmetry visible in lateral section.

Figures 19, 20, 21, 22, 23:
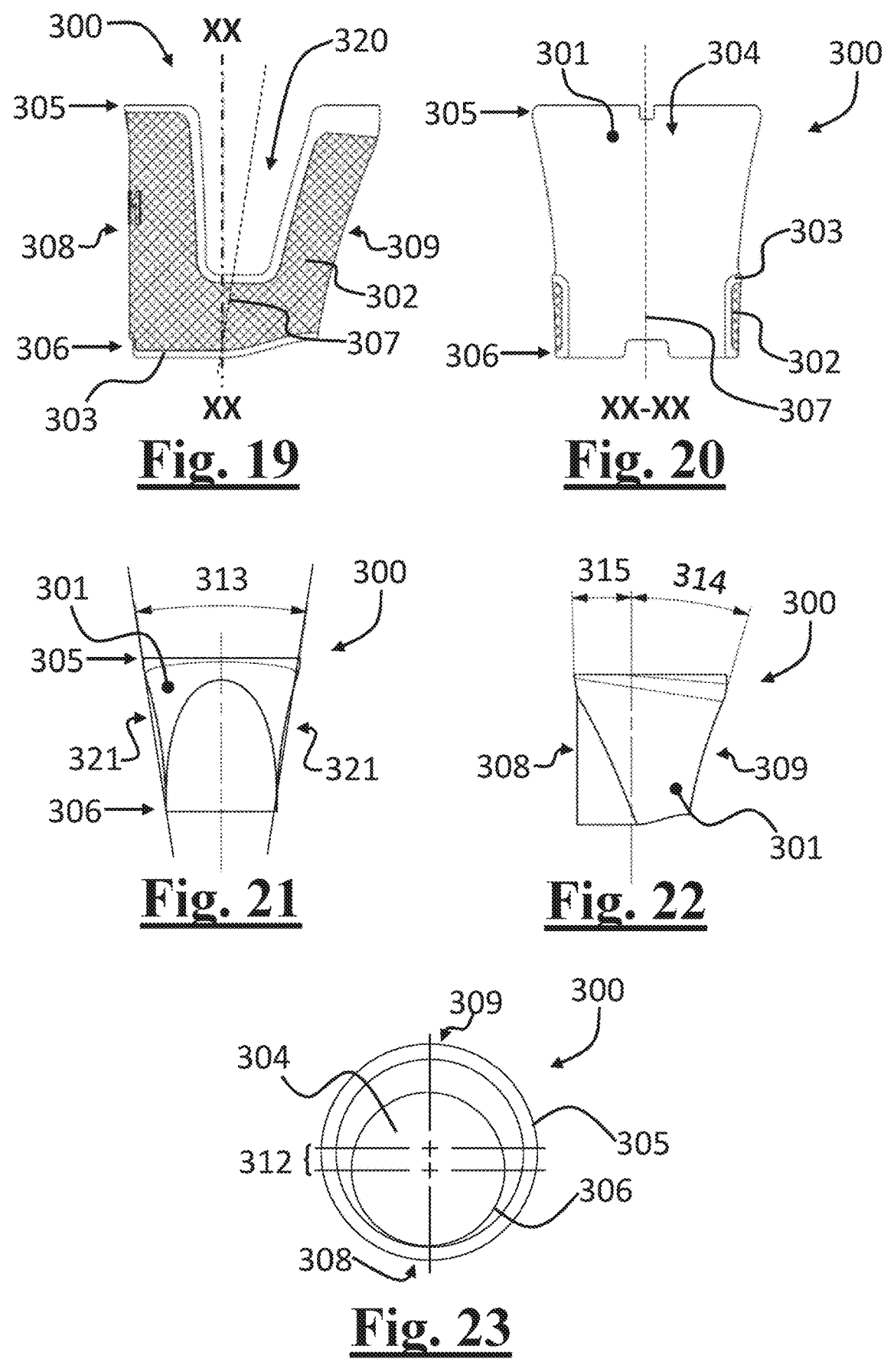

FIG. 19 shows a lateral view of the augment element 300 for prosthesis, wherein some features already discussed in relation to FIG. 18 are pointed out.

For tibial applications, it can be seen that the first transversal section at the end 305 is larger in size with respect to the second transversal section at the end 306, so as to facilitate an insertion of said metal body into the tibial bone extremity.

The augment element 300 further comprises a pair of cut-outs 320 arranged sideways in the metal body 301, and open from the first end 305 up to an intermediate portion on the metal body 301.

FIG. 20 shows a frontal sectional view of the augment element 300 for prosthesis, with respect to section XX-XX of FIG. 19.

In this embodiment, it is appreciated how the longitudinal axis 307 of the cavity 304 is instead not inclined with respect to a vertical axis of the metal body 301, considering the direction transversal to the direction of inclination shown in FIG. 18.

FIG. 21 shows a frontal view of the augment element 300 for prosthesis with geometrical indications relating to the metal body 301.

Preferably, the metal body 301 comprises lateral walls 321 at the cut-outs 320; such lateral walls 321 have respective curved and concave shapes with respect to the outside of the metal body 301, to replicate a medial/side and rear bone anatomy.

In particular, an overall conicity 313 of the symmetric lateral walls 321, measured with respect to imaginary straight lines passing through the two edges of the metal body 301, respectively at the first end 305 and the second end 306, is overall comprised between 12° and 20°, more preferably equal to 18°.

FIG. 22 shows a lateral view of the augment element 300 for prosthesis with geometrical indications relating to the metal body 301.

In the example of the augment element 300, the frontal wall 308 is near the vertical, with an inclination 315 equal to 2° with respect to the vertical. In general, an inclination of the frontal wall 308 with respect to the vertical axis can be comprised between 0° and 5°, more preferably comprised between 0° and 2°.

In the example of the augment element 300, the rear wall 309 has an inclination of 16° with respect to the vertical. In general, an inclination of the rear wall 309 with respect to the vertical axis is comprised between 15° and 20°.

Preferably, the rear wall 309 further has a curved and concave shape with respect to the outside of the metal body 301, to replicate a tibial bone rear anatomy.

FIG. 23 shows a top view of the augment element 300 for prosthesis.

In this view, it is possible to appreciate the eccentricity 312 resulting between the first transversal section (in this case, circular) at the first end 305 and the second transversal section (in this case, circular) at the second end 306 of the axial through-cavity 304.

FIG. 24 shows a prospective view of a fourth embodiment of augment element 400 for prosthesis according to the present invention. The augment element 400 of this example is an element for tibial application, in combination with a knee prosthesis.

The augment element 400 comprises a metal body 401 of a substantially truncated conical shape, which is configured to be inserted in a tibial extremity. Preferably, the metal body 401 is made of titanium or alloys thereof, for biomedical applications.

The metal body 401 has an outer surface comprising a metal trabecular surface 402; preferably the metal trabecular surface 402 is directly applied to the metal body 401 by a co-manufacture procedure, made in one piece and seamlessly, for example by EBM (Electron Beam Machining) technologies.

The metal body 401 preferably comprises a smooth edge 403 on the outer surface surrounding the metal trabecular surface 402 on one or more sides, preferably on all sides.

The metal body 401 is hollow with an axial through-cavity 404 defining a plurality of substantially annular transversal sections, whose configuration will be further described.

FIG. 25 shows a frontal view of the augment element 400 for prosthesis, wherein the two symmetric lateral walls 421 of the same are shown, having a same inclination and configuration.

FIG. 26 shows a lateral sectional view of the augment element 400 for prosthesis, with respect to section XVI-XVI of FIG. 25.

The metal body 401 is inclined in a direction of inclination, in this case towards the right of the figure, so as to define at least one eccentricity between a first transversal section at a first end 405 of the axial through-cavity 404 and a second transversal section at a second end 406 of the axial through-cavity 404.

In particular, the axial cavity 404 has a longitudinal axis 407 inclined in the direction of inclination with respect to a vertical axis of the metal body 401. The vertical axis, not shown in the figure for the sake of simplicity, is perpendicular to one of the first or second transversal section, at the respective end 405 or 406.

The metal body 401 comprises a frontal wall 408 extended towards the direction of inclination and a rear wall 409 opposite the frontal wall 408 and extended away from the direction of inclination.

The frontal wall 408 has an inclination with respect to the vertical axis that is less than an inclination of the rear wall 409.

In other words, the profile of the metal body 401 is tapered towards the second end 406, with a frontal asymmetry visible in lateral section.

FIG. 27 shows a lateral view of the augment element 400 for prosthesis, wherein some features already discussed in relation to FIG. 26 are pointed out.

For tibial applications, it can be seen that the first transversal section at the end 405 is larger in size with respect to the second transversal section at the end 406, so as to facilitate an insertion of said metal body into the tibial bone extremity.

The augment element 400 further comprises a pair of cut-outs 420 arranged sideways in the metal body 401, and open from the first end 405 up to an intermediate portion on the metal body 401.

FIG. 28 shows a frontal sectional view of the augment element 400 for prosthesis, with respect to section XXVIII-XXVIII of FIG. 27.

In this embodiment, it is appreciated how the longitudinal axis 407 of the cavity 404 is instead not inclined with respect to a vertical axis of the metal body 401, considering the direction transversal to the direction of inclination shown in FIG. 26.

FIG. 29 shows a top view of the augment element 400 for prosthesis, wherein it is appreciated that the first transversal section at the end 405 is bilobed annular, such that the outer surface of the metal body 401 is tapered between the first transversal section and the second transversal section, as better visible in FIG. 24.

In a natural analogy, the metal body 401 is similar to a flower corolla shape from which two opposed petals were removed.

In this view, it is also possible to appreciate the double eccentricity 412 resulting between the first transversal section (in this case, bilobed therefore having two circumference centres which describe it) at the first end 405, and the second transversal section (in this case, circular with only one circumference centre) at the second end 406 of the axial through-cavity 404.

FIG. 30 shows a frontal view of the augment element 400 for prosthesis for prosthesis with geometrical indications relating to the metal body 401.

Preferably, the metal body 401 comprises lateral walls 421 at the cut-outs 420; such lateral walls 421 have respective curved and concave shapes with respect to the outside of the metal body 401, to replicate a medial/side and rear bone anatomy.

In particular, an overall concavity 413 of the lateral symmetric walls 421 is overall comprised between 45° and 55°, more preferably equal to 50°.

FIG. 31 shows a lateral view of the augment element 400 for prosthesis with geometrical indications relating to the metal body 401.

In the example of the augment element 400, the frontal wall 408 is near the vertical, with an inclination 415 equal to 2° with respect to the vertical. In general, an inclination of the frontal wall 408 with respect to the vertical axis can be comprised between 0° and 5°, more preferably comprised between 0° and 2°.

In the example of the augment element 400, the rear wall 409 has an inclination of 19.4° with respect to the vertical. In general, an inclination of the rear wall 409 with respect to the vertical axis is comprised between 15° and 20°.

Preferably, the rear wall 409 further has a curved and concave shape with respect to the outside of the metal body 401, to replicate a tibial bone rear anatomy.

FIGS. 32 and 33 show respective prospective views of a variation of the augment element 400' for prosthesis.

In this variation, the augment element 400' comprises a plurality of through-slits 410 in the metal body, open from the first end up to a intermediate portion on the metal body, which are configured for a radial compression of the metal body, locally reducing a circumference during insertion of the augment element 400', and increasing a press-fit towards a bone portion. Preferably, each of the slits 410 ends in a respective enlarged circular hole 411.

Figure 34:
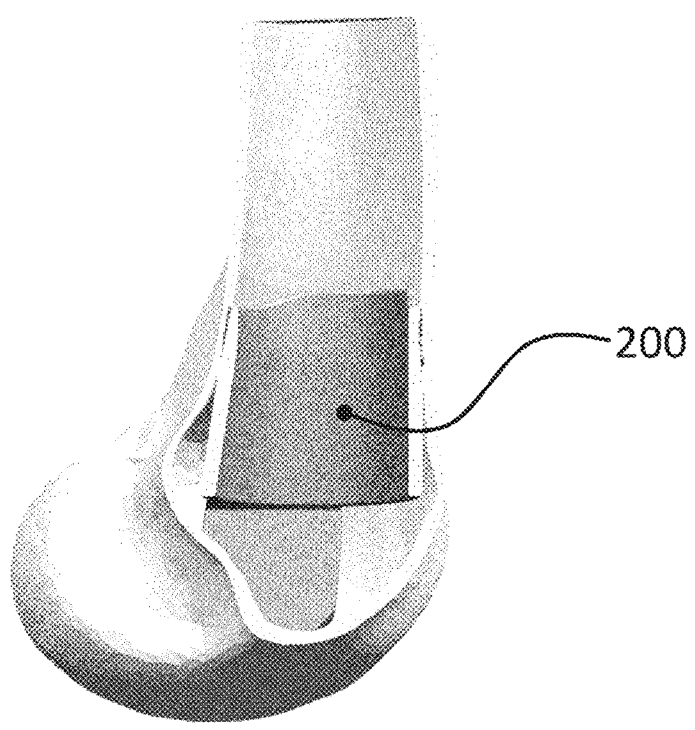
FIG. 34 shows an example of application of the second embodiment of augment element for prosthesis to a femoral extremity.

FIG. 34 shows an example of application of the augment element 200 for prosthesis to a femoral extremity.

Figure 35:
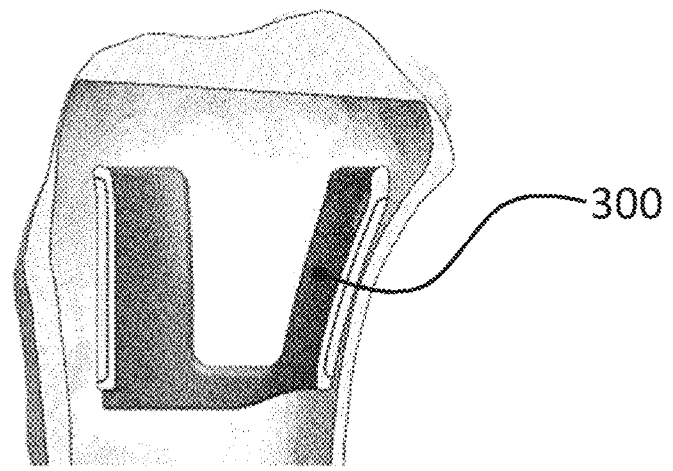
FIG. 35 shows an example of application of the third embodiment of augment element for prosthesis to a tibial extremity.

FIG. 35 shows an example of application of the augment element 300 for prosthesis to a tibial extremity.

It is clear that further implementations and modifications of the present invention will be possible for the person skilled in the art, in order to meet contingent needs.

In particular, specific features described with reference to an embodiment could be also applied to other embodiments described herein in a variation thereof, if there is no technical prejudice in this regard.

The above-described embodiments are therefore to be understood as provided for illustrative and non-limiting purpose.

The invention claimed is:

1. An augment element for knee prosthesis, comprising a metal body of a substantially truncated conical shape configured to be inserted into a bone extremity and having an outer surface comprising a metal trabecular surface, said metal body being hollow with an axial through-cavity defining a plurality of substantially annular transversal sections, wherein said metal body is inclined in a direction of inclination, so as to define at least one eccentricity between a first transversal section at a first end of said axial through-cavity and a second transversal section at a second end of said axial through-cavity, said augment element further comprising a plurality of through-slits in said metal body, said through-slits being open from said first end up to an intermediate portion on said metal body, wherein said plurality of through-slits is configured for a radial compression of said metal body, locally reducing a circumference of said substantially annular transversal sections during insertion of said augment element and increasing a press-fit towards a bone portion.

2. The augment element according to claim 1, wherein said axial cavity has a longitudinal axis inclined in said direction of inclination with respect to a vertical axis of said metal body, said vertical axis being perpendicular to one of said first or second transversal section.

3. The augment element according to claim 2, wherein said metal body comprises a frontal wall extending towards said direction of inclination and further comprises a rear wall opposite said frontal wall and extended away from said direction of inclination, wherein said frontal wall has an inclination with respect to said vertical axis that is less than an inclination of said rear wall.

4. The augment element according to claim 1, wherein for femoral applications said first transversal section is smaller in size with respect to said second transversal section, so as to facilitate an insertion of said metal body into a femoral bone extremity.

5. The augment element according to claim 1, wherein each of said plurality of through-slits ends in a respective enlarged circular hole beside to said intermediate portion, said enlarged circular hole being configured to improve a localized mechanical resistance of said metal body.

6. The augment element according to claim 1, for femoral applications wherein said first transversal section is smaller in size with respect to said second transversal section, and further comprising a pair of bicondylar supports arranged sideways in said metal body, each of said bicondylar supports protruding from said second transversal section and comprising a tapered body widening away from said metal body.

7. The augment element according to claim 6, wherein said bicondylar supports have an outer surface comprising a metal trabecular surface made in one piece and seamlessly with said bicondylar supports.

8. The augment element according to claim 6, wherein said second transversal section is inclined in a second direction of inclination which is transversal to said direction of inclination, and wherein said pair of bicondylar supports extends from said second transversal section by a same height, thus defining an asymmetric pair of bicondylar supports.

9. The augment element according to claim 1, wherein said metal body comprises a smooth edge on said outer surface surrounding said metal trabecular surface.

10. The augment element according to claim 1, wherein said metal trabecular surface is made in one piece and seamlessly with said metal body.

11. The augment element according to claim 1, wherein said metal body comprises walls having a substantially constant thickness.

* * * * *